United States Patent [19]

Gunasekera et al.

[11] Patent Number: 5,059,618

[45] Date of Patent: Oct. 22, 1991

[54] NOVEL BIOACTIVE DISCODERMIDES AND METHODS OF USE

[75] Inventors: Sarath P. Gunasekera; Malika Gunasekera; Peter J. McCarthy, all of Vero Beach, Fla.

[73] Assignee: Harbor Branch Oceanographic Institution, Inc., Fort Pierce, Fla.

[21] Appl. No.: 548,783

[22] Filed: Jul. 6, 1990

[51] Int. Cl.$^5$ ................... C07D 309/14; A61K 31/365
[52] U.S. Cl. ...................................... 514/410; 540/462
[58] Field of Search .......................... 514/410; 540/462

[56] References Cited

U.S. PATENT DOCUMENTS

| | | | |
|---|---|---|---|
| 4,548,814 | 10/1985 | Rinehart, Jr. | 530/317 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |

OTHER PUBLICATIONS

Faulkner, D. J. (1986), Natural Products Reports 1:551–598.
Faulkner, D. J. (1986), 3:1–33.
Faulkner, D. J. (1987), Natural Products Reports 4:539–576.
Uemura, D., K. Takahashi, T. Yamamoto; C. Katayama, J. Tanaka, Y. Okumura, Y. Hirata (1985), "Norhalichondrin A: An Antitumor Polyether Macrolide from a Marine Sponge," J. Am. Chem. Soc. 107:4796–4798.
Kato, Y., N. Fusetani, S. Matsunaga, and K. Hashimoto (1986), "Calyculin A, a Novel Antitumor Metabolite from the Marine Sponge *Discodermia calyx*," J. Am. Chem. Soc. 108:2780–2781.
Matsunaga, S., N. Fusetani, and S. Konosu (1984), "Bioactive Marine Metabolites VI. Structure Elucidation of Discodermin A, an Antimicrobial Peptide From the Marine Sponge *Discodermia kiiensis*," Tetrahedron Letters 25(45):5165–5168.
Matsunaga, S., N. Fusetai, and S. Konosu (1985), "Bioactive Marine Metabolites VII. Structures of Discodermins B, C, and D, Antimicrobial Peptides from the Marine Sponge *Discodermia kiiensis*," Tetrahedron Letters 26(7):855–856.
Kato, Y., N. Fusetani, S. Matsunaga, and K. Hashimoto (1988), "Isolation and Structure Elucidation of Calyculins B, C, and D, Novel Antitumor Metabolites from the Marine Sponge *Discodermia calyx*," J. Org. Chem. 53:3930–3932.

*Primary Examiner*—Mukund J. Shah
*Assistant Examiner*—Y. N. Gupta
*Attorney, Agent, or Firm*—Saliwanchik & Saliwanchik

[57] ABSTRACT

A novel lactam discodermide has been isolated from a marine sponge. This compound, and its derivatives, are useful as antifungal and antitumor agents.

13 Claims, No Drawings

NOVEL BIOACTIVE DISCODERMIDES AND METHODS OF USE

BACKGROUND OF THE INVENTION

Considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed. The prevention and control of fungi is also of considerable importance to man, and much research has been devoted to development of antifungal measures.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge *Theonella* sp.; and U.S. Pat. No. 4,737,510 discloses compounds, having antiviral and antibacterial properties, isolated from the Caribbean sponge *Agelas coniferin*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978–1983, Vol. I–V; Faulkner, D. J., (1984) Natural Products Reports 1:551–598; Natural Products Reports (1986) 3:1–33; Natural Products Reports (1987) 4:539–576; J. Am. Chem. Soc. (1985) 107:4796–4798.

The subject invention concerns novel lactam discodermides. The parent compound was isolated from the marine sponge *Discodermia dissoluta*. This sponge has been previously reported in the literature. See Kato, Y., N. Fusetani, S. Matsunaga, and K. Hashimoto (1986) J. Am. Chem. Soc. 108:2780; Matsunaga, S., N. Fusetani, and S. Konosa (1984) Tetrahedron Letters 25:5165; Matsunaga, S., N. Fusetani, and S. Konosa (1985) Tetrahedron Letters 26:855; Kato, Y., N. Fusetani, S. Matsunaga, K. Hashimoto, and K. Koseki (1988) J. Org. Chem. 53:3930. The compounds claimed here have never before been described. The present invention, utilizing sponges as a source material has provided the art with a new class of biologically active compounds and new pharmaceutical compositions useful as antitumor and antifungal agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns novel lactam discodermides and methods of use for these compounds. Specifically exemplified are discodermide and discodermide acetate, and various derivatives of these compounds. The structure of these compounds is shown below.

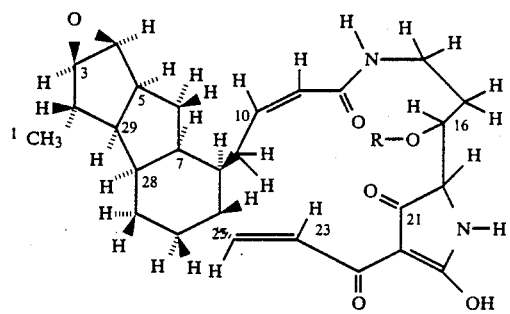

Discodermide: R = H
Discodermide acetate: R = COCH$_3$

These compounds have been found to inhibit tumor cell growth and are, therefore, useful in the treatment of cancer in animals and humans.

These compounds have also been found to inhibit fungal growth and, therefore, can be used in the treatment of certain diseases in humans, animals, and plants.

DETAILED DISCLOSURE OF THE INVENTION

The subject invention pertains to a novel chemical compound isolated from marine sponges as well as its derivatives. These compounds have been shown to possess antitumor and antifungal activity. Thus, the subject invention pertains to the compounds themselves, as well as pharmaceutical compositions containing these compounds. Also disclosed and claimed are methods for administering the novel compositions. The derivatives of these compounds can be produced by known procedures. The parent compound can be isolated from marine sponges as described below.

The isolation of the natural product was performed using solvent partition followed by chromatography. The final purification of the novel compound can be achieved either by crystallization or by using HPLC. The structure of this compound was determined mainly on the basis of its $^1$H and $^{13}$C NMR data.

The compounds of the subject invention, including derivatives thereof, have antitumor and antifungal properties. Thus, they can be used for the treatment of a number of diseases including cancer.

Following are examples which illustrate procedures, including the best mode, for practicing the invention. These examples should not be construed as limiting. All percentages are by weight and all solvent mixture proportions are by volume unless otherwise noted.

EXAMPLE 1

Identification and Location of Marine Sponge

The sponge of interest was collected in Lucay, Grand Bahama Island, Bahamas. The sponge was found at a depth of 100 feet. The sponge has been classified as follows:

| Phylum: | Porifera |
| Genus: | Discodermia |
| Species: | *dissoluta* |

The sponge is brown-purple to beige-tan and is common in this location.

EXAMPLE 2

Isolation of Compounds

The sponge *Discodermia dissoluta* (434 g) was homogenized with methanol toluene (3:1). After filtration and evaporation at reduced pressure below 35° C., a brown colored extract (22.1 g, 5.0% wet weight) was obtained. The extract was then partitioned between EtOAc and $H_2O$. The water soluble fraction was repartitioned between BuOH and $H_2O$. Concentration of the BuOH soluble fraction yielded a brown solid (18.2 g, 4.1% wet weight). A portion of the brown solid (60 g) was chromatographed on reversed phase C-18 (64 g, Lichroprep RP-18, 40–63 μm) using MeOH—$H_2O$ gradient. The fraction that eluted with 10 to 20% $H_2O$/MeOH gave impure discodermide. Crystallization from MeOH/$CH_2Cl_2$(3:2) gave pure discodermide as a white powder, 155 mg (0.1% from frozen sponge).

EXAMPLE 3

Characterization of Discodermide

Decomposes ~200° C., $(\alpha)D$ 97.5° (c=0.2, $CHCl_3$/MeOH, 1:1); UV $\lambda_{max}$ (MeOH) 313 nm (ε=9,650), 238 (16,500); IR (KBr) 3350, 2910, 2460, 1695, 1600, 1465, 1227, 995, and 840 $cm^{-1}$; $^1H$ NMR ($d_5$-Py) δ9.13 (1H, br s, H13), 9.02 (1H, s, H18), 8.28 (1H, d, J=15.2 Hz, H23), 6.97 (H, dd, J=15.2, 10.3 Hz, H24), 6.62 (1H, br s, OH16), 6.28 (1H, d, J=11.5 Hz, H11), 6.03 (1H, dd, J=11.5, 7.1 Hz, H10), 4.84 (1H, br s, H16), 4.40 (1H, s, H17), 4.13 (1H, m, H9), 4.06 (1H, m, H14), 3.31 (1H, s, H4), 3.26 (1H, s, H3), 3.20 (1H, m, H14), 2.49 (1H, m, H5), 2.44 (1H, m, H15), 2.31 (1H, d, J=16.7 Hz, H9), 2.03 (1H, m, H25), 1.95 (H, m, H2), 1.90 (1H, m, H6), 1.64 (1H, m, H27), 1.60 (1H, m, H15), 1.49 (H, m, H26), 1.45 (1H, m, H29), 1.26 (2H, m, H6, 7), 1.07 (3H, m, H8, 26, 28), 0.79 (3H, d, J=7.0 Hz, H1), 0.73 (1H, m, H27); $^{13}C$ NMR ($CDCl_3$/$CD_3OD$ 3:1) δ193.5 (s, C19), 183.9 (s, C22), 178.5 (s, C21), 167.2 (s, C12), 147.5 (d, C24), 141.3 (d, C10), 128.1 (d, C23), 123.0 (d, C11), 101.1 (s, C20), 70.6 (d, C16), 66.7 (d, C3), 66.5 (d, C17), 61.3 (d, C4), 57.5 (d, C29), 50.8 (d, C28), 47.3 (d, C7), 45.6 (d, C25), 44.1 (d, C8), 41.2 (d, C5), 36.5 (t, C14), 36.2 (d, C2), 32.2 (t, C26), 30.6 (t, C6), 30.2 (t, C27), 29.7 (t, C15), 29.4 (t, C9), 17.7 (q, C1); HRFABMS: m/z 505.2312, Δ 0.7 mmu for $C_{27}H_{34}N_2O_6Na$; LRFABMS (Thio) m/z (Relative Intensity) 505 (58%), 313 (17), 239 (23), 217 (100), 181 (34).

EXAMPLE 4

Preparation and Characterization of Discodermide Acetate and Other Derivatives Acetylation of discodermide with acetic anydride and pyridine at room temperature furnished discodermide acetate: colorless gum; $(\alpha)D$ 77.5° (C=0.17, MeOH); UV $\lambda_{max}$ (EtOH) 312 nm (ε 9,660), 238 (16,500); IR (KBr) 3360, 2910, 2500, 1724, 1655, 1600, 1465, 1380, 1240, 1015, and 845 $cm^{-1}$; $^1H$ NMR ($d_6Py$) δ9.25 (1H, t, J=5.8 Hz, H13), 9.20 (1H, s, H18), 8.25 (1H, d, J=15.3 Hz, H23), 6.98 (1H, dd, J=15.3, 10.3 Hz, H24), 6.32 (1H, d, J=11.5 Hz, H11), 6.03 (1H, dd, J=11.5, 7.1 Hz, H10), 5.82 (1H, d, J=5.9 Hz, H16), 4.36 (1H, s, H17), 4.15 (1H, ddd, J=12.8, 12.0, 1.5 Hz, H9), 3.95 (1H, m, H14), 3.32 (1H, s, H4), 3.27 (1H, s, H3), 3.09 (H, ddd, J=11.0, 9.8, 1.5 Hz, H14), 2.47 (1H, m, H5), 2.40 (1H, m, H15), 2.27 (1H, d, J=11.5 Hz, H9), 1.98 (1H, m, H25), 1.93 (1H, m, H2), 1.90 (1H, m, H6), 1.80 (3H, s, H31), 1.65 (1H, m, H27), 1.62 (1H, m, H15), 1.56 (1H, m, H26), 1.49 (1H, m, H29), 1.27 (2H, m, H6, 7), 1.09 (3H, m, H8, 26, 28), 0.79 (3H, d, J=7.0 Hz, H1), 0.73 (1H, m, H27); $^{13}C$ NMR ($d_5$-Py) δ192.6 (s, C19), 184.3 (s, C22), 180.5 (s, C21), 170.5 (s, C30), 167.3 (s, C12), 147.3 (d, C24), 140.3 (d, C10), 129.8 (d, C23), 125.1 (d, C11), 102.5 (s, C20), 75.4 (d, C16), 66.3 (d, C3), 65.1 (d, C17), 61.1 (d, C4), 58.2 (d, C29), 51.4 (d, C28), 47.9 (d, C7), 45.7 (d, C25), 45.0 (d, C8), 41.9 (d, C5), 37.4 (t, C14), 36.9 (d, C2), 33.2 (t, C26), 30.9 (t, C6), 30.3 (t, C27), 29.8 (t, C15), 29.3 (t, C9), 20.9 (q, C31), 18.2 (q, C1); LRFABMS: (Thio) m/z (Rel. Int.) 547 (100%, $(M+Na)^+$), 525 (25, $(M+H)^+$), 505 (20), 487 (55), 469 (15), 429 (18), 319 (34).

Other modifications of discodermide can readily be made by those skilled in the art. For example, O-alkylation with alkylating agents gives monoalkylated discodermide wherein R is a lower alkyl ($C_1$ to $C_5$). The 10- and 23-diepoxide derivative can be prepared by treatment with metachloroperbenzoic acid. The 10- and 23-tetrahydro derivative can be prepared by catalytic hydrogenation using $PtO_2H_2O$. The dilute acid hydrolysis product is the 3- and 4-dihydroxy derivative.

EXAMPLE 5

Antifungal Properties

A. Protocol

1. Preparation of Inocula

*Candida albicans: C. albicans* (ATCC strain 44506) was grown on Sabouraud dextrose agar to produce single colonies, one of which was used to inoculate Sabouraud dextrose broth. The broth was incubated at 37° C. with shaking at 200 rpm for 18 hours. The resultant culture was brought to 10% (v/v) glycerol, frozen at −80° C., and used as the inoculum for the anti-Candida assay.

2. Assay Protocols i. Disc diffusion assay

*C. albicans* was inoculated into either melted Sabouraud dextrose agar or Roswell Park Memorial Institute medium 1640 (RPMI-1640) in 2% agar at 45° C. to give a cell density of approximately 10,000 cells/mL. Plates were prepared with 10 mL of the needed agar in a 10 cm × 10 cm petri dish. These plates were stored at 4° C. until needed for the assay.

Paper discs (6.35 mm) were impregnated with the test substance and allowed to dry. They were then placed onto the surface of a test plate prepared as detailed above. Plates were incubated overnight at 37° C., after which time the zones of growth inhibition could be read. These are expressed as the diameter of the zone in millimeters. Standard drugs were used in all cases.

3. MIC Protocol

Two-fold dilutions of the drug/extract were prepared in 50 λL volumes of a suitable solvent using 96-well microtiter plates. A 25% mixture of MeOH in water was generally used; however, EtOH, 5% EtOAc in EtOH, DMSO, or other compatible solvents could be substituted if necessary. In a separate 96-well plate, 35

μL volumes of either Sabouraud dextrose broth or RPMI-1640 were placed in each well. The drug/extract (5 μL) was then transferred to the broth using a 12-place pipettor. An inoculum of *C. albicans* in the appropriate medium was added to give a cell density of 1000 cells/mL and a total volume of 50 μL. If DMSO was used as solvent a total volume of 100 μL was used so that the DMSO level did not exceed 5%. SDB plates were incubated at 37° C. overnight, RPMI-1640 plates were incubated at 37° C. in a humidified atmosphere of 10% $CO_2$. 10 μL of triphenyl tetrazolium chloride (1% w/v; filter sterilized) was then added to each well; a further 2 hour incubation resulted in a deep coloration of the microorganism. The MIC is the lowest concentration of the drug which has completely inhibited growth.

B. Results

Discodermide was found to inhibit the growth of fungi such as *Candida albicans*. The antifungal activity may be of use in the treatment of fungal diseases of humans, animals, and plants. Formulations may be for either topical or systemic use.

The minimum dose required for activity against *C. albicans* (MIC) is 12.5 μg/ml.

EXAMPLE 6

P388 Mouse Leukemia Cell Assay

A. Maintenance of Cell Line

P388 murine leukemia cells obtained from Dr. J. Mayo, National Cancer Institute, Bethesda, MD, were maintained in Roswell Park Memorial Institute medium 1640 (RPMI-1640) supplemented with 10% horse serum and cultured in plastic tissue culture flasks and kept in an incubator at 37° C. in humidified air containing 5% $CO_2$. Antibiotic-free stock cultures of P388 cells were subcultured to $10^5$ cells/ml by dilutions in fresh growth medium at 2 to 5 day intervals.

B. Procedure

To assess the antiproliferative effects of agents against P388 cells, 200 μl cultures (96-well tissue culture plates, Nunc, Denmark) were established at $1 \times 10^5$ cells/ml in drug-free medium containing agents at various concentrations. After 48 hour exposures, P388 cells were enumerated using 3-[4,5-dimethylthiazol-2-yl]-2,5-diphenyltetrazolium bromide (MTT) as described below.

To quantitate the effects of agents on cell proliferation, 75 μl warm growth medium containing 5 mg/ml MTT was added to each well. Cultures were returned to the incubator and left undisturbed for 90 minutes. To spectrophotometrically quantitate formation of reduced formazan, plates were centrifuged (900 g, 5 minutes), culture fluids were removed by aspiration, and 200 μl of acidified isopropanol (2 ml concentrated HCl/L isopropanol) added per well. The absorbance of the resulting solutions were measured at 570 nm with a plate reader (MR700 Microplate Reader, Dynatech Laboratories, Chantilly, Va.). The absorbance of test wells was divided by the absorbance of drug free wells, and the concentration of the agent that resulted in 50% of the absorbance of untreated cultures was determined by linear regression of logit-transformed data. A linear relationship between P388 cell number and formazan production was found over the range of cell densities observed in this study.

C. Results

Discodermide was found to have strong inhibitory properties against mouse leukemia cells in vitro and to have an $IC_{50}$ of 0.4 μg/ml. The antitumor $IC_{50}$ of discodermide acetate was found to be 14.0 μg/ml. The compound itself or a composition derived from it may be used for inhibiting tumors in humans or in animals.

EXAMPLE 7

Formulation and Administration

The compounds of the invention are useful for various non-therapeutic and therapeutic purposes. It is apparent from the testing that the compounds of the invention are effective for inhibiting fungal growth and for controlling tumor growth. Also, because of the antifungal properties of the compounds, they are useful to swab laboratory benches and equipment in a microbiology laboratory to eliminate the presence of fungi, or they can be used as ultraviolet screeners in the plastics industry since they effectively absorb UV rays. As disclosed herein, they are also useful prophylactically and therapeutically for treating fungal infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

We claim:

1. A compound having the following structure:

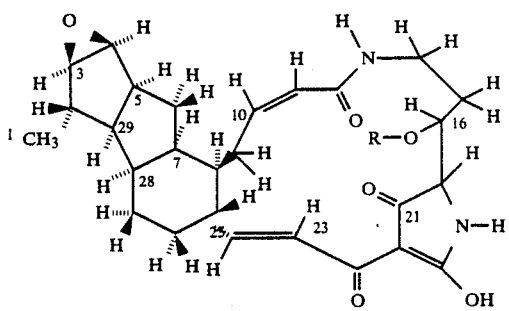

wherein R is H, lower alkyl, or COCH₃; or a derivative of said compound.

2. The compound, according to claim 1, wherein R is H.

3. The compound, according to claim 1, wherein R is COCH₃.

4. The compound, according to claim 1, wherein R is CH₃.

5. A process for treating a human or animal hosting leukemia cells, said process comprising administering to said human or animal a leukemia cell inhibiting amount of a compound having the following structure:

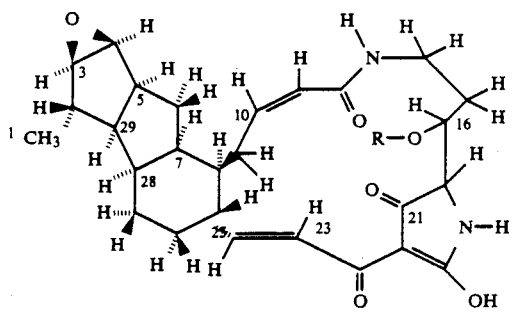

wherein R is H, lower alkyl, or COCH₃; or a derivative of said compound.

6. The process, according to claim 5, wherein for said compound, R is H.

7. The process, according to claim 5, wherein for said compound, R is COCH₃.

8. The process, according to claim 5, wherein for said compound, R is CH₃.

9. A process for inhibiting fungal growth, said process comprising the administration to said fungus or location where said fungus is growing, of an effective fungal inhibiting amount of a compound having the following structure:

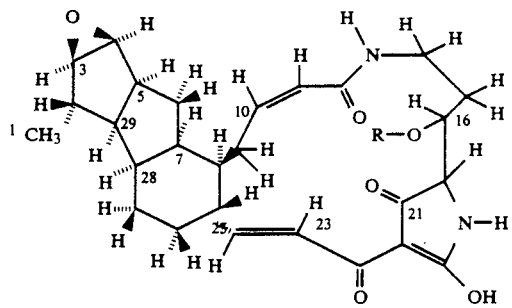

wherein R is H, lower alkyl, or COCH₃; or a derivative of said compound.

10. The process, according to claim 9, wherein for said compound, R is H.

11. The process, according to claim 9, wherein for said compound, R is COCH₃.

12. The process, according to claim 9, wherein for said compound, R is CH₃.

13. A pharmaceutical composition for the inhibition of leukemia cell growth or fungal growth, said composition comprising an appropriate pharmaceutical carrier and a compound having the following structure:

wherein R is H, lower alkyl, or COCH₃; or a derivative of said compound.

* * * * *

UNITED STATES PATENT AND TRADEMARK OFFICE
CERTIFICATE OF CORRECTION

PATENT NO.   : 5,059,618

DATED        : October 22, 1991

INVENTOR(S)  : Sarath P. Gunasekera, Malika Gunasekera, Peter J. McCarthy

It is certified that error appears in the above-identified patent and that said Letters Patent is hereby corrected as shown below:

Column 3:  Line 66: "($d_6 P_4$)" should read --($d_6$-Py)--.
Column 4:  Line 64: "50 $\lambda$L" should read --50 $\mu$L--.

Signed and Sealed this

Thirtieth Day of March, 1993

*Attest:*

STEPHEN G. KUNIN

*Attesting Officer*  Acting Commissioner of Patents and Trademarks